United States Patent [19]

Pool

[11] Patent Number: 4,592,747
[45] Date of Patent: Jun. 3, 1986

[54] FLUID FLOW SENSOR

[75] Inventor: Scott L. Pool, Santa Ana, Calif.

[73] Assignee: Parker-Hannifin Corporation, Cleveland, Ohio

[21] Appl. No.: 621,573

[22] Filed: Jun. 18, 1984

[51] Int. Cl.⁴ ............................................. A61M 5/005
[52] U.S. Cl. ..................................... 604/246; 73/715; 116/270; 137/557
[58] Field of Search ............... 604/246, 245, 247, 118; 128/675; 73/715, 730; 137/557; 116/270

[56] References Cited

U.S. PATENT DOCUMENTS 3,880,151 4/1975 Nilsson et al. ..................... 73/715
4,398,542 8/1983 Cunningham et al. ............. 128/675

Primary Examiner—John D. Yasko
Attorney, Agent, or Firm—Frederick L. Tolhurst

[57] ABSTRACT

A flow sensor wherein a body (10) that includes a recessed surface (18) is covered by a flexible cover (12). The portion of flexible cover (12) adjacent recessed surface (18) moves between a contracted position and an expanded position to indicate flow.

14 Claims, 4 Drawing Figures

FLUID FLOW SENSOR

BACKGROUND OF THE INVENTION

1. Field of the Invention

The subject invention is directed to flow sensors and, more particularly, to flow sensors suitable for use in medication dispensing systems.

2. Description of the Prior Art

Over the years, various types of medication dispensing systems have been developed. Generally, these systems provide for delivery of medication from a variety of pressure chambers or pumps through a catheter and into the patient. Examples are shown and described in U.S. Pat. Nos. 3,951,147; 4,193,397; 4,360,019; and 4,373,527. Such systems are, however, subject to various failure modes such as a stalled pump condition, or an occlusion in the catheter. Such failures have been particularly troublesome where the delivery rate of medication is so low that the user is unaware of the interruption of medication flow until the physiological symptoms develop.

Accordingly, there was a need in the prior art for a device that would indicate the fluid flow condition in various types of medication delivery systems. Because of the potentially harmful consequences of interruptions in medication delivery, it was most important that such a flow sensor be reliable. However, such sensors would typically be applied to systems having at least some disposable components so that it was also important that the flow sensor could be inexpensively manufactured. Moreover, many such systems are carried by the patients on a daily basis in the normal course of their activities. These systems are compact and highly portable so that a compatible flow sensor would also need to be similarly compact and portable.

Various types of fluid pressure measuring devices were known in the prior art. For example, U.S. Pat. No. 4,398,542 is directed to a pressure measuring device wherein pressure of fluid flow between a flexible membrane and a body is sensed by a pressure transducer. Other examples of pressure measuring devices are shown in U.S. Pat. Nos. 4,185,641; 3,240,207; and 1,861,999. However, none of those devices afforded a suitably reliable yet inexpensive flow sensor that was sufficiently compact for use in a wide range of medication dispensing systems.

Some medication delivery systems have employed various schemes for providing audible or visual alarms in response to over-pressure conditions. However, these were pressure-sensitive arrangements that were not responsive to flow conditions. Indeed, they generally required a substantial pressure accumulation to activate the alarm. Moreover, the benefit of such alarms was seriously compromised for patients having visual or auricular disabilities.

Consequently, various methodologies for detecting medication flow were developed. For example, the user of a portable medication dispensing device would occasionally remove the needle from his body to observe whether medication was, in fact, flowing. Such methodologies were, at best, uncomfortable and awkward for the user. Moreover, they tended to expose the medication system to contamination and the patient to infection.

Accordingly, there was a need in the prior art for a flow sensor that was inexpensive, reliable, and suitable for use on medication infusion devices. Preferably, such a sensor would provide a tangibly perceptive indication of flow conditions.

SUMMARY OF THE INVENTION

In accordance with the subject invention, a fluid flow sensor includes a body with a flexible cover secured thereto. The body includes a recessed surface that is located between input and output ends with internal passages through the body communicating between the recessed surface and the input and output ends. The flexible cover is movable between contracted and expanded positions in response to changes in fluid flow through the internal passages.

Specifically, the flexible cover is tensioned such that it is normally urged toward the contracted position where it contacts the recessed surface, but is maintained in an expanded position where it is apart from the recessed surface in response to fluid flow through the internal passages. Under normal fluid flow conditions, the expanded position of the flexible cover is generally located at a radius intermediate the radius of the peripheral surface of the body and the radius of the recessed surface. Under occluded fluid flow conditions, the expanded position of the flexible cover is generally located at a radius adjacent the radius of the peripheral surface of the body.

Preferably, the body has a generally cylindrical shape with the recessed area being a saddle-shaped surface having a planar central surface with adjoining convex surfaces at oppositely disposed edges. Also preferably, the fluid flow sensor includes tubes that are respectively secured to recesses in the input and output ends of the body and communicate with the first and second passages.

Other details, objects and advantages of the subject invention will become apparent from the following description of a presently preferred embodiment thereof.

BRIEF DESCRIPTION OF THE DRAWINGS

The accompanying drawings show a presently preferred embodiment of the subject invention wherein.

DESCRIPTION OF THE PREFERRED EMBODIMENT

Figure 1:
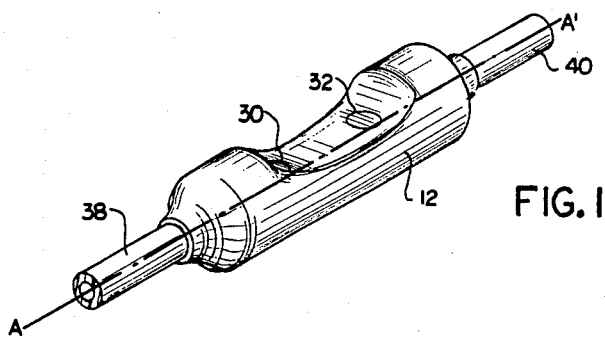
FIG. 1 is a perspective view of the subject fluid flow sensor.

As shown in FIGS. 1–4, the fluid flow sensor of the subject invention includes a body 10 that is enveloped in a flexible cover 12. While body 10 can have various other general shapes and sizes, in the preferred embodiment, body 10 is of a generally cylindrical shape aligned along a central longitudinal axis A—A'. Body 10 includes an input end 14 and an output end 16 at oppositely disposed, longitudinal ends thereof. Body 10 also includes a generally cylindrical peripheral surface that is located at radius $R_2$ from the central axis A—A'.

Body 10 further includes a recessed surface 18 having a planar surface 20 and adjoining convex surfaces 22 and 24. Planar surface 20 is tangentially located with respect to the central longitudinal axis A—A' at a radius $R_1$ that is less than the radius $R_2$. Planar surface 20 intersects the cylindrical surface of body 10 and adjoins convex surfaces 22 and 24 at oppositely disposed sides thereof. Convex surfaces 22 and 24 provide a continuous surface between the adjoining edge of planar surface 20 and the peripheral surface of body 10 such that recessed surface 18 forms a saddle-shaped surface.

Body 10 further includes recesses 26 and 28 respectively located in input end 14 and output end 16. Passages 30 and 32 are also included in body 10. Passage 30 provides fluid communication between recessed surface 18 and recess 26. Passage 32 provides fluid communication between recessed surface 18 and recess 28. More specifically, passage 30 intersects recessed surface 18 to form a port 34 in planar surface 20 adjacent the intersection with convex surface 22. Passage 32 intersects recessed surface 18 to form port 36 in planar surface 20 adjacent the intersection with convex surface 24.

Tubes 38 and 40 are secured in recesses 26 and 28 respectively to link the disclosed flow sensor to the rest of the fluid system. Thus, passage 30 provides fluid communication between recessed surface 18 and tube 38 and passage 32 provides fluid communication between recessed surface 18 and tube 40.

Flexible cover 12 is comprised of a medical-grade, heat-shrink tubing selected from a group of materials including polyvinyl chloride. Flexible cover 12 envelops body 10 and is secured thereto through a commercially known heat-shrinking process such that its constricts about body 10 and is under tension across recessed surface 18. Flexible cover 12 is a thin-wall material having a specified tensile strength and elasticity over a range of intended flow conditions for the fluid stream.

Figure 2:
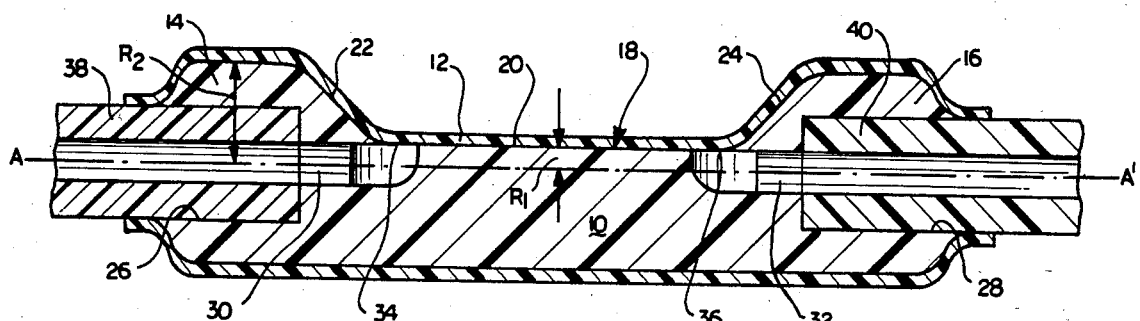
FIG. 2 is a cross-section of the sensor of FIG. 1 taken along longitudinal axis A—A' and showing the cover in a contracted state.
Figure 4:
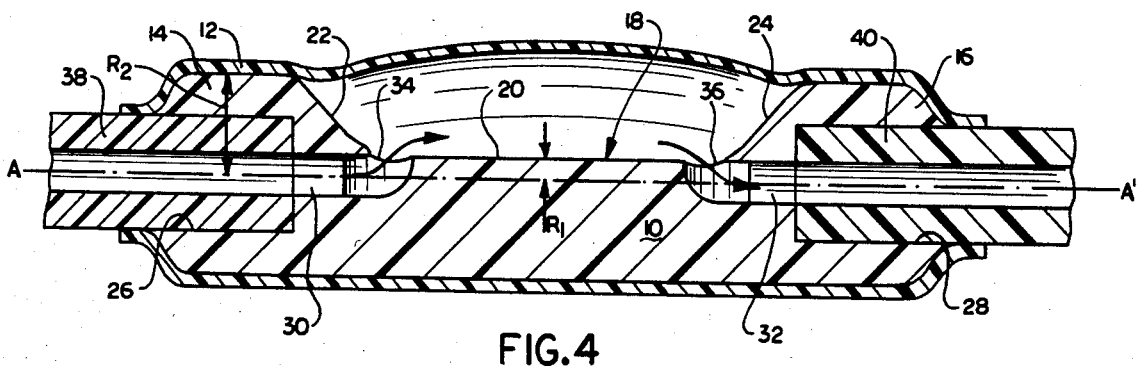
FIG. 4 is a cross-section of the sensor as shown in FIG. 2 except that the cover is in an expanded state that indicates occluded flow.

As particularly shown in FIGS. 2, 2 and 4, flexible cover 12 is moved between a contracted position and an expanded position. FIG. 2 shows the contracted position of flexible cover 12 wherein it contacts recessed surface 18 between ports 34 and 36 and is substantially parallel to planar surface 20. Thus, with flexible cover 12 in the contracted position, flexible cover 12 is substantially planar and there is no path for fluid flow between port 34 of passage 30 and port 36 of passage 32.

Figure 3:
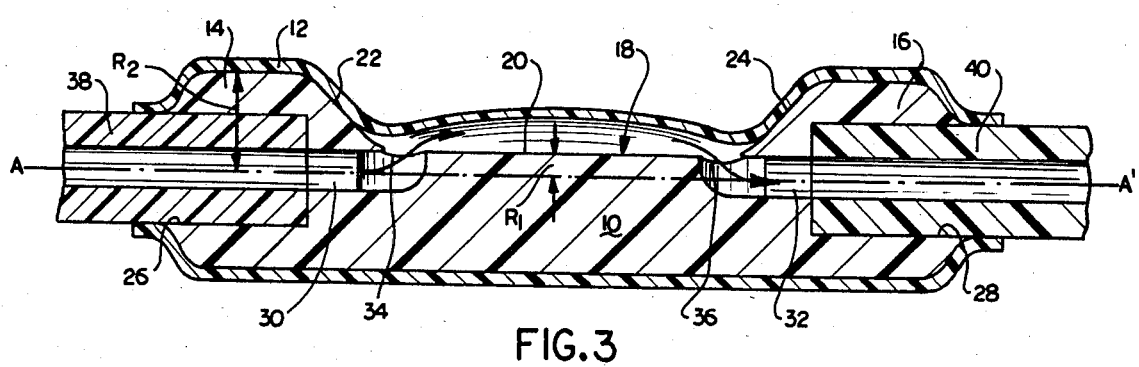
FIG. 3 is a cross-section of the sensor as shown in FIG. 2 except that the cover is in an expanded state that indicates normal flow.

Under normal flow conditions, the fluid separates flexible cover 12 from contact with recessed surface 18 as shown in FIG. 2, and moves it into an expanded position apart from recessed surface 18 as shown in FIG. 3. In the expanded position of FIG. 3, flexible cover 12 is removed part from planar surface 20 in a generally convex or dome shape. In this expanded position, flexible cover 12 is located at a radius intermediate radius $R_2$ of the peripheral surface of body 10 and radius $R_1$ of recessed surface 18. Thus, a flow path between ports 34 and 36 is established.

Under occluded flow conditions, the fluid separates flexible cover 12 from contact with recessed surface 18 and moves it into an expanded position apart from recessed surface 18 as shown in FIG. 4. In FIG. 4, flexible cover 12 is generally at a radius adjacent radius $R_2$ of the peripheral surface of body 10.

Accordingly, flow conditions through the disclosed sensor can be detected by monitoring the position of flexible cover 12 in the region of recessed surface 18. When flexible cover 12 is continuously adjacent recessed surface 18, there is no flow, but when flexible cover 12 is expanded away from recessed surface 18, the sensor detects normal or occluded flow conditions.

In the operation of the preferred embodiment, fluid flow in the fluid path in which the sensor is incorporated causes substantial movement of flexible cover 12 such that flow conditions can be monitored manually. Specifically, a patient holds the sensor between his thumb and index finger to sense the relative movement of flexible cover 12 with respect to the body 10. A convex shape of cover 12 in the region of planar surface 20 of recessed surface 18 indicates that flow conditions exist in the sensor. A planar shape of cover 12 in the region of planar surface 20 indicates that fluid flow conditions do not exist.

Thus, as applied to intermittent or pulsed-flow systems, the disclosed sensor will indicate that no flow is established at the pump by remaining constantly planar as shown in FIG. 2. However, the sensor will indicate that normal or expected flow conditions are established through the fluid path being monitored by pulsing between its contracted position shown in FIG. 2 and its expanded position shown in FIG. 3 in accordance with the pulsed flow. The disclosed sensor will indicate a downstream occlusion of the flow path by constantly remaining in its expanded position as shown in FIG. 4.

While a presently preferred embodiment of the subject invention is shown and described herein, the subject invention is not limited thereto, but can be otherwise variously embodied within the scope of the following claims:

I claim:

1. A fluid flow sensor comprising:
    a body having an input end and an output end with a recessed surface located therebetween, said body further including a first internal passage between said input end and said recessed surface, and a second internal passage between said output end and said recessed surface;
    a flexible cover that is secured to said body, said flexible cover being movable between a contracted position and an expanded position in response to fluid flow through said first and second internal passages, said flexible cover contacting the recessed surface in said contacted position and being spaced apart from the recessed surface in said expanded position.

2. The fluid flow sensor of claim 1 wherein said first internal passage forms a first port in said recessed surface and said second internal passage forms a second port in said recessed surface, and wherein said flexible cover is tensioned such that it is normally urged toward contact with the recessed surface between said first and second ports.

3. The fluid flow sensor of claim 1 or 2 wherein said flexible cover is secured to said body adjacent the perimeter of said recessed surface.

4. The fluid flow sensor of claim 2 wherein said recessed surface is a saddle-shaped surface comprising:
    a planar surface; and
    first and second convex surfaces that adjoin the planar surface at oppositely disposed edges thereof.

5. The fluid flow sensor of claim 4 wherein said first and second ports are respectively located adjacent the junctions between the planar surface and said first and second convex surfaces.

6. The fluid flow sensor of claim 5 further comprising:

first and second tubes that are respectively secured to the input and output ends of said body, and are respectively in communication with said first and second passages.

7. The fluid flow sensor of claim 6 wherein said first and second tubes are secured to said body by an adhesive.

8. The fluid flow sensor of claim 6 wherein said flexible cover is secured to said first and second tubes.

9. The fluid flow sensor of claim 1 wherein the expanded position of the flexible cover is located at a radius adjacent the radius of the peripheral surface of the body during occluded flow conditions.

10. The fluid flow sensor of claim 1 or 9 wherein the expanded position of the flexible cover under normal flow conditions is located at a radius intermediate the radius of the peripheral surface of the body and the radius of said recessed surface.

11. The fluid flow sensor of claim 10 wherein said flexible cover is generally dome-shaped in its expanded position.

12. A fluid flow sensor comprising:
a generally cylindrical body having recesses on opposite ends thereof, said body further including a saddle surface with a first passage between said saddle surface and one of said recesses and a second passsage between said saddle surface and the other of said recesses;
a first length of tubing secured in one of said recesses and a second length of tubing secured in the other of said recesses; and
a flexible cover that envelopes said body and is secured at opposite ends of said body adjacent said recesses, said cover being in tension across the saddle surface between the first and second passages such that said cover is contracted against said saddle surface when there is no fluid flow between said first and second passages and is expanded away from said saddle surface when there is fluid flow between said first and second passages.

13. The fluid flow sensor of claim 12 wherein said body is comprised of a polycarbonate material.

14. The flow sensor of claim 12 or 13 wherein said cover is comprised of thin wall polyvinyl chloride tubing have a tensile strength less than the tensile strength of said hose.

* * * * *